(12) United States Patent
Pasquet et al.

(10) Patent No.: US 9,084,637 B2
(45) Date of Patent: Jul. 21, 2015

(54) INTERVERTEBRAL IMPLANT

(75) Inventors: Denis Pasquet, Quinsac (FR); Jaques Senegas, Merignac (FR); Regis Le Couedic, Bordeaux (FR)

(73) Assignee: Zimmer Spine, Bordeaux (FR)

( * ) Notice: Subject to any disclaimer, the term of this patent is extended or adjusted under 35 U.S.C. 154(b) by 1733 days.

(21) Appl. No.: 12/280,901

(22) PCT Filed: Feb. 27, 2007

(86) PCT No.: PCT/FR2007/050852
§ 371 (c)(1),
(2), (4) Date: Jun. 1, 2010

(87) PCT Pub. No.: WO2007/099258
PCT Pub. Date: Sep. 7, 2007

(65) Prior Publication Data
US 2010/0256680 A1 Oct. 7, 2010

(30) Foreign Application Priority Data

Feb. 28, 2006 (FR) ...................................... 06 50687

(51) Int. Cl.
*A61B 17/70* (2006.01)
(52) U.S. Cl.
CPC .......... *A61B 17/7062* (2013.01); *A61B 17/7053* (2013.01)
(58) Field of Classification Search
CPC ........... A61B 17/7053; A61B 17/7062; A61B 17/7071
USPC ................... 606/246, 248, 249, 263, 90, 105; 623/17.11
See application file for complete search history.

(56) References Cited

U.S. PATENT DOCUMENTS

| 6,419,676 | B1 * | 7/2002 | Zucherman et al. .......... 606/249 |
| 6,626,944 | B1 * | 9/2003 | Taylor ........................ 623/17.16 |
| 2001/0016743 | A1 | 8/2001 | Zucherman et al. |
| 2003/0045935 | A1 * | 3/2003 | Angelucci et al. ......... 623/17.11 |
| 2003/0050700 | A1 * | 3/2003 | Kihara ...................... 623/17.11 |
| 2004/0117017 | A1 * | 6/2004 | Pasquet et al. ............. 623/17.11 |
| 2005/0004674 | A1 * | 1/2005 | Senegas et al. ............ 623/17.13 |
| 2005/0143738 | A1 * | 6/2005 | Zucherman et al. ........... 606/61 |

(Continued)

FOREIGN PATENT DOCUMENTS

| FR | 2 799 640 | 4/2001 |
| FR | 2 870 107 | 11/2005 |

(Continued)

*Primary Examiner* — Jan Christopher Merene
*Assistant Examiner* — Atiya Mahmud
(74) *Attorney, Agent, or Firm* — Seager, Tufte & Wickhem, LLC

(57) ABSTRACT

An intervertebral implant comprising an intervertebral spacer and two fastener ties is disclosed. The intervertebral spacer may be formed having a body extending in a longitudinal direction. The intervertebral spacer may further include a first insertion face, a second face, and two recesses disposed at the ends of the body. The recesses may each be defined by a first extension, a second extension, and an end wall. Each of the two fastener ties may be secured to the first extension at a first end and a second end may be fastenable to the second face. The ties may pass around a spinous process in part and hold the spinous process within a recess. The first extension of the body may have a height relative to the bottom wall of the recess that is no greater than the height of the second extension.

12 Claims, 2 Drawing Sheets

(56) References Cited

U.S. PATENT DOCUMENTS

| | | | |
|---|---|---|---|
| 2005/0165398 A1* | 7/2005 | Reiley | 606/61 |
| 2005/0203512 A1* | 9/2005 | Hawkins et al. | 606/61 |
| 2005/0228383 A1* | 10/2005 | Zucherman et al. | 606/61 |
| 2005/0245937 A1* | 11/2005 | Winslow | 606/90 |
| 2007/0149972 A1* | 6/2007 | Nakajima et al. | 606/61 |
| 2007/0191832 A1* | 8/2007 | Trieu | 606/61 |
| 2008/0033556 A1* | 2/2008 | Le Couedic et al. | 623/17.16 |

FOREIGN PATENT DOCUMENTS

| | | | | |
|---|---|---|---|---|
| WO | WO 02/051326 | | 7/2002 | |
| WO | WO 02/071960 | | 9/2002 | |
| WO | WO2005/120277 | * | 12/2005 | A61B 17/70 |

* cited by examiner

INTERVERTEBRAL IMPLANT

The present invention provides an intervertebral implant constituted by a spacer for placing between the spinous processes of two consecutive vertebrae, together with ties for securing the ends of the spacer to said process. More particularly, the invention relates to such an implant designed to be put into place laterally relative to the plane defined by the patient's spine that is to receive the implant.

Such implants provided with intervertebral spacers are described in particular in French patent application 01/03362 and in French patent application 04/05064 in the name of the Applicant.

Putting such a spacer into place raises certain problems associated with surgical practice. The so-called supraspinous ligament interconnects all of the tips of the spinous processes with one another. To enable the spacer to be put into place it is necessary to move the ligament. In practice, it is detached from the two processes concerned and it is moved away by means of a suitable surgical instrument. A scalpel is used to detach the ligament from the processes. Once the spacer has been put into place, the ligament is stitched back onto the processes after making a small opening therein for receiving the stitching suture.

The major drawback of that surgical practice is that by acting on the ligament so as to detach and move it away, the ligament is caused to lose its mechanical properties. Furthermore, all those operations take time, thereby lengthening the surgical duration of the surgery.

Usually, when it is necessary to proceed with total ablation of the natural intervertebral disk, it is necessary to have access to said disk axially, and thus the above-described surgical practice cannot be avoided.

Nevertheless, certain circumstances exist in which the situation is different. This applies when it is necessary to ablate a disk hernia, which operation requires access only from one side of the spinal column. Under such circumstances, it would be particularly advantageous to have an intervertebral implant in which the spacer can be put into place easily via a lateral approach between the spinous processes, since the surgery proper does not itself require any more than that approach.

This is not possible with the spacers of known intervertebral implants because the prongs on either side of the recess for receiving the spinous process are of relatively large height, typically at least 5 millimeters (mm). Such a prong height would require an unacceptable amount of distraction to be applied to the two vertebrae concerned.

An object of the present invention is to provide an intervertebral implant for placing between spinous processes and that can be put into place laterally without presenting the above-mentioned drawbacks.

To achieve this object, according to the invention, the intervertebral implant for placing between the spinous processes of two adjacent vertebrae comprises:

an intervertebral spacer formed as a single part comprising a body having a longitudinal direction, presenting in said direction an insertion first face and a second face, and two recesses disposed at the longitudinal ends of the body, each recess being defined by a first extension extending said insertion face, by a second extension extending the second face of the body, and by an end wall; and two means forming fastener ties, each tie-forming means presenting a first end secured to said first extension of the body, and a second end fastenable to said second face to pass around a spinous process in part and hold it in the recess.

The implant is characterized in that each first extension of the body presents a height relative to the bottom wall of the recess that is no greater than that of the second extension associated therewith, and that lies in the range 1 mm to 3 mm.

It will be understood that because each first extension of the spacer defining the top and bottom recesses presents a height that is reduced compared with the height of known implants, it is much easier to put the spacer into place laterally between the spinous processes, since the amount by which the processes need to be spaced apart is reduced.

The inventors have shown that, because of the action of the ligaments, this reduced height does not disturb retention of the process in the recess.

These characteristics make it possible to have taller second extensions, thus encouraging retention of the process in the recess of the spacer, in particular in co-operation with the fastener ties.

Preferably, the height of the first extension of the spacer body is less than 80% or preferably less than 60% of the height of the second extension, thereby making it effectively easier to put the spacer into place laterally since this limits the spacing apart that is required between the processes.

Also preferably, the height of the first extension of the spacer body is greater than 30%, or preferably greater than 50%, of the height of the second extension, thereby ensuring that the spinous processes are held effectively in the recesses defined by the pairs of extensions of the spacer body.

Preferably, the implant further comprises blocking means for blocking the second end of the tie-forming means, said blocking means being fastenable in releasable manner on the second face of said body.

It should be understood that this disposition makes it easier for surgeons to block and tension the ties after they have been put into place around the spinous processes.

Also preferably, the insertion face of the spacer body is a portion of a cylindrical surface having generator lines that are parallel to the generator lines defining the inside walls of the recesses.

This characteristic makes it easier to insert the spacer laterally between the two spinous processes, because of the shape of the insertion face and because of the cylindrical shape thereof.

Other characteristics and advantages of the invention appear better on reading the following description of an embodiment given by way of non-limiting example. The description refers to the accompanying figures, in which.

Figure 1A:
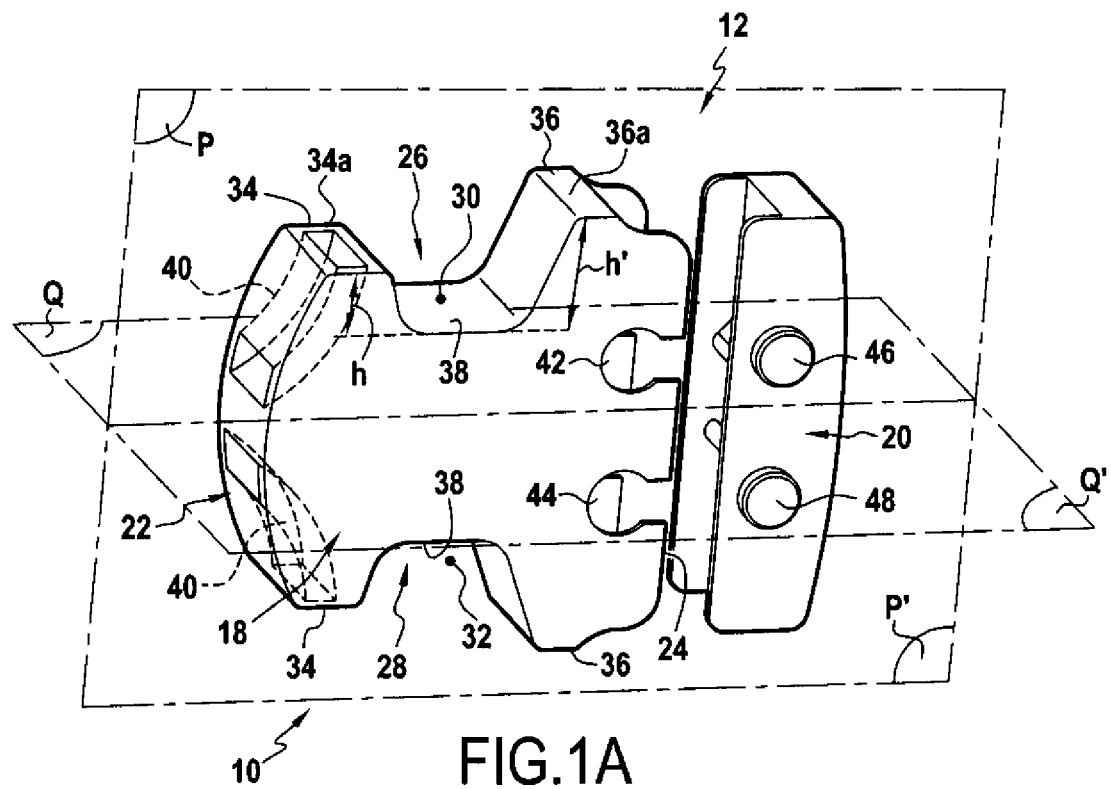
FIG. 1A is a perspective view of the spacer in which the tie-blocking member is not secured to the spacer body.
Figure 1B:
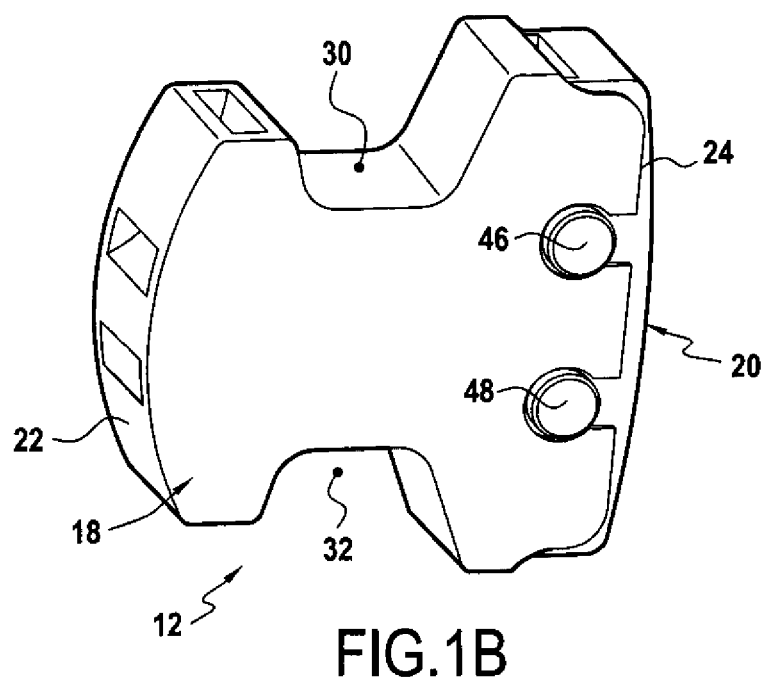
FIG. 1B is a similar view showing the tie-blocking member clipped onto the spacer body.

With reference initially to FIGS. 1A and 1B, the structure of the intervertebral spacer is described. The intervertebral implant, referenced 10, is preferably constituted by an intervertebral spacer 12 and by two fastener ties 14 and 16 visible in FIGS. 2 and 3. The intervertebral spacer 12 is preferably constituted by a body 18, e.g. made of polyetheretherketone (PEEK), and by a tie-blocking member 20 which, in this embodiment, is removable from the body of the spacer. Nevertheless, it would not go beyond the invention if the tie-blocking means were to form an integral portion of the spacer body 18.

The spacer body 18 has a midplane PP' about which the body is symmetrical. The body 18 has an insertion first face 22 and an opposite second face 24. In the embodiment described, the blocking member 20 is fastened on the second face 24. The insertion face 22 is preferably in the form of a portion of a convex cylindrical surface having generator lines that are orthogonal to the midplane PP' and that correspond substantially to a portion of the circular cylindrical surface. The spacer body has a second midplane QQ' orthogonal to the first midplane PP'.

At its two opposite ends 26 and 28, the spacer body 18 presents in known manner respective recesses 30 and 32 for receiving the spinous processes. Each recess is defined by two extensions or prongs 34 and 36, the extensions 34 extending the insertion face 22 of the spacer body, and the extensions 36 extending the second face 34 of the spacer body. Each recess 30, 32 also has an end wall 38. The inside wall of each recess is a ruled surface having generator lines parallel to the second midplane QQ'.

According to an essential characteristic of the invention, the first extensions 34 closer to the insertion face of the spacer are of a height h that is no greater than the height h' of the second extensions 36 closer to the second face 24 of the spacer body. The term "height of the extensions" should be understood as the distance in the midplane PP' between the end wall 38 of the recess and the tips 34a, 36a of the extensions.

The height h' is preferably the standard height for conventional extensions of a spacer body, i.e. it is not less than 5 mm. The height h of the first extensions is preferably less than 80%, more preferably less than 60% of the height h' of the second extensions in order to make it easier to insert the spacer between spinous processes. In contrast, and also preferably, the height h is at least 50%, or preferably 30% of the height h' so as to define recesses 30, 32 that are of depth that is sufficient to hold the spinous processes mechanically in the recesses.

In any event, the height h of the first extensions lies in the range 3 mm to 1 mm.

The first extensions 34 also include an internal passage 40 that opens out respectively into the tip 34a of the extension and into the insertion face 22. By means of this passage, the first end 16a, 14a of each tie can be secured to the spacer body close to its insertion face 22.

To tension and the ties 14 and 16 and block them in tension, the spacer is fitted, as mentioned above, with a blocking member 20 that, in the embodiment described, can be fastened releasably on the second face 24 of the spacer body. For this purpose, the spacer body close to its face 24 may include two pairs of elastically deformable recesses 42 and 44 suitable for co-operating with clip-fastener studs 46 and 48 formed in the faces of the blocking member 20 parallel to the midplane PP'.

Figure 3:
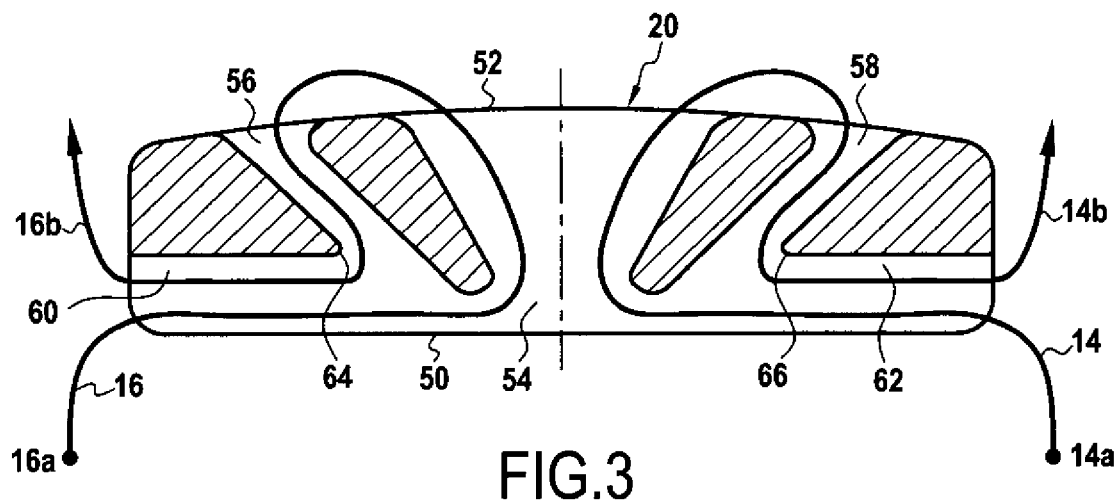
FIG. 3 is a longitudinal section view of a preferred embodiment of the tie-blocking member.

With reference now to FIG. 3, there follows a brief description of a preferred embodiment of the blocking member 20, this blocking member being described in detail in French patent application 04/05064.

The blocking member 20 is constituted by a part that presents a first face 50 for co-operating with the second face 24 of the spacer body, and an opposite face 52. In the part forming the blocking member 20, there is provided an axial slot 54 that extends between the faces 50 and 52 of the blocking member and that is of a shape that flares from the face 50 towards the face 52. The part constituting the blocking member also has two symmetrical side slots referenced 56 and 58. Finally, this part defines passages 60 and 62 for passing the ties 14 and 16. Each passage 60 and 62 co-operates with the side slots 56, 58 to define a rubbing edge 64, 66.

In FIG. 3, there can be seen the path of each tie 14 and 16 in the various slots of the blocking member 20. When the blocking member 20 is locked on the spacer body, by exerting traction on the free ends 16b and 14b of the ties 16 and 14, these ties are put under tension and they are self-blocking so as to hold the spinous processes in the recesses 30 and 32 of the spacer.

Figure 2:
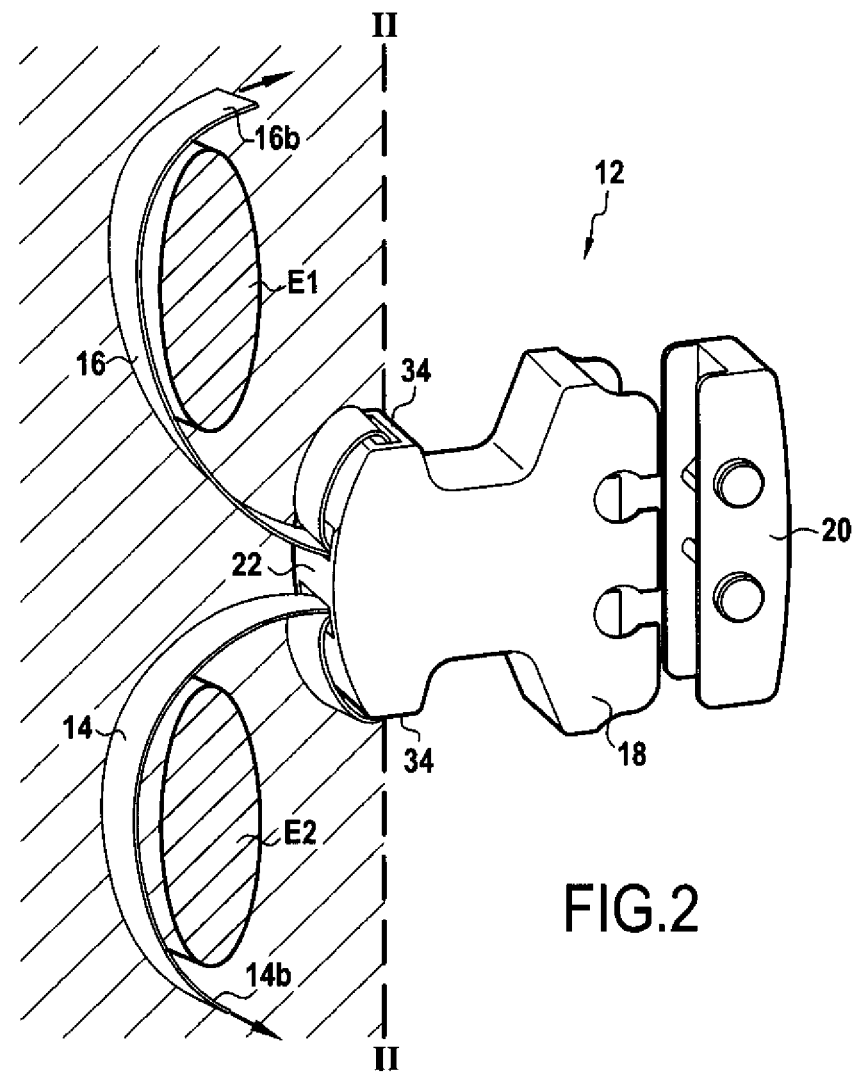
FIG. 2 is a perspective view of the spacer showing how the spacer is put into place between the spinous processes.

With reference now to FIG. 2, there follows a description of the surgical technique for putting the implant 10 into place.

To put the implant into place, the surgeon performs the following steps.

An incision II is made slightly to the right of the axis of the patient's spine. The shaded portion represents the zone that is masked by the patient's skin. Thereafter the surgeon moves away the muscles on the right in a rightward direction through a distance of about 3 centimeters (cm) to 4 cm. In the following step, the surgeon removes the intra-spinous ligament. Once these operations have been performed, the surgeon inserts into the incision the free ends of the ties 14 and 16 and causes them to pass around the spinous processes E1 and E2. The surgeon then returns these free ends back out through the incision. The surgeon then inserts the spacer body into the incision between the spinous processes, presenting the insertion face 22 initially. As explained above, because the extensions 34 corresponding to the insertion face of the spacer body are of reduced height, a reduced amount of spacing apart is required between the spinous processes. In addition, the cylindrical shape of the insertion face facilitates putting the spacer between the processes. Once the spinous processes have entered into the recesses in the spacer body, the surgeon inserts the free ends of the ties into the various passages of the blocking member 20 and causes the blocking member 20 to be clipped onto the space 24 of the spacer body. It then suffices to exert appropriate traction on the free ends 16b, 14b of the two ties in order to achieve self-blocking clamping of the ties on the spinous processes.

Preferably, the insertion face 22 of the body is a cylindrical surface having generator lines that are parallel to the generator lines defining the inside walls of the recesses 30, 32.

Also preferably, in the longitudinal direction, the body 18 has a middle portion and two end portions in which said recesses 30 and 32 are defined, the end portions presenting a higher degree of stiffness than the middle portion.

Also preferably, each tie-forming means 14, 16 is constituted by a strip of flexible material.

The invention claimed is:

1. An intervertebral implant for placing between the spinous processes of two adjacent vertebrae, the implant comprising:
   an intervertebral spacer formed as a single part comprising a body having a longitudinal direction, presenting in said direction an insertion first face and a second face, and two recesses disposed at opposing ends along the longitudinal direction of the body, each recess being defined by a first extension extending from said insertion face, by a second extension extending from the second face of the body, and by an end wall;
   a first fastener tie having a first end and a second end, the first end secured to at least one of the first extensions of the body and a second end fastenable to the second face of the body;

a second fastener tie having a first end and a second end, the first end secured to at least one of the first extensions of the body and a second end fastenable to the second face of the body; and a single blocking means for blocking the second ends of both the first and second fastener ties together, said blocking means being fastenable in a releasable manner on the second face of said body;

wherein each first extension of the body presents a total height relative to the end wall of the recess that is less than a total height of each second extension, and that lies in the range of 1 mm to 3 mm.

2. An implant according to claim 1, wherein the total height of each first extension of the body is less than 80% of the total height of each second extension.

3. An implant according to claim 2, wherein the total height of each first extension of the body is greater than 30% of the total height of each second extension.

4. An implant according to claim 1, wherein the spacer presents a plane of symmetry orthogonal to the longitudinal direction, and wherein said insertion face presents a convex shape that is symmetrical about said plane of symmetry.

5. An implant according to claim 1, wherein said blocking means comprises a system for automatically blocking the second end of one of the first or second fastener ties.

6. An implant according to claim 1, wherein said body comprises, in the longitudinal direction, a middle portion and two end portions in which said recesses are defined, the end portions presenting rigidity greater than that of the middle portion.

7. An implant according to claim 1, wherein each of the fastener ties is constituted by a strip of flexible material.

8. An intervertebral implant for placing between the spinous processes of two adjacent vertebrae, the implant comprising:

an intervertebral spacer comprising a body having a longitudinal direction, the body having a first recess disposed at a first longitudinal end and a second recess disposed at a second longitudinal end wherein the first recess is defined by a first extension extending along a first face of the body and a second extension extending along a second face of the body and the second recess is defined by a third extension extending along the first face of the body and a fourth extension extending along the second face of the body;

a first fastener tie having a first end and a second end, the first end secured to the first extension of the body and the second end fastenable to the second face of the body;

a second fastener tie having a first end and a second end, the first end secured to the third extension of the body and the second end fastenable to the second face of the body; and a single blocking means for blocking the second ends of both the first and second fastener ties together, the blocking means being fastenable in a releasable manner on the second face of said body;

wherein the first extension of the body and the third extension each have a total height relative to a bottom wall of the recess that is less than a total height of both the second and fourth extensions; and wherein the spacer presents a plane of symmetry orthogonal to the longitudinal direction, and wherein the first face presents a convex shape that is symmetrical about the plane of symmetry.

9. The intervertebral implant of claim 8, wherein the total height of each of the first and third extensions is between 1 millimeter and 3 millimeters.

10. The intervertebral implant of claim 9, wherein the total height of the first extension is less than 80% of the total height of the second extension and wherein the total height of the third extension is less than 80% of the total height of the fourth extension.

11. The intervertebral implant of claim 10, wherein the total height of the first extension is greater than 30% of the total height of the second extension and wherein the total height of the third extension is greater than 30% of the total height of the fourth extension.

12. The intervertebral implant of claim 8, wherein the body comprises, in the longitudinal direction, a middle portion and two end portions in which the recesses are defined, the end portions having a rigidity greater than that of the middle portion.

\* \* \* \* \*